(12) United States Patent
Johnson et al.

(10) Patent No.: US 10,347,114 B2
(45) Date of Patent: Jul. 9, 2019

(54) MOISTURE SENSING SYSTEM

(71) Applicant: Parker-Hannifin Corporation, Cleveland, OH (US)

(72) Inventors: Thomas G. Johnson, Manchester, MO (US); Raghujit Prasad Kunapuli, Saint Charles, MO (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 15/996,653

(22) Filed: Jun. 4, 2018

(65) Prior Publication Data

US 2018/0357884 A1    Dec. 13, 2018

Related U.S. Application Data

(60) Provisional application No. 62/516,745, filed on Jun. 8, 2017, provisional application No. 62/607,462, filed on Dec. 19, 2017.

(51) Int. Cl.
G08B 21/00 (2006.01)
G08B 21/20 (2006.01)
(Continued)

(52) U.S. Cl.
CPC .......... *G08B 21/20* (2013.01); *G01N 21/251* (2013.01); *G01N 21/29* (2013.01); *G01N 21/81* (2013.01);
(Continued)

(58) Field of Classification Search
None
See application file for complete search history.

(56) References Cited

U.S. PATENT DOCUMENTS 5,341,649 A * 8/1994 Nevitt .................. F25B 41/006
                                                    62/126
5,935,334 A * 8/1999 Fong ................. H01J 37/32192
                                                  118/723 ME
(Continued)

FOREIGN PATENT DOCUMENTS

| JP | S5480190 A | 6/1979 |
|----|-----------|--------|
| WO | 9323739 A1 | 11/1993 |
| WO | 2017083613 A1 | 5/2017 |

OTHER PUBLICATIONS

Parker-Hannifin Corporation, Wet-Tec Electronic Moisture Sensor & Sight Glass and Moisture Indicators Brochure, 2 pages, www.frigodesign.ru/sale/parker/Sight_Glass_Parker.pdf.
(Continued)

*Primary Examiner* — Julie B Lieu
(74) *Attorney, Agent, or Firm* — Renner, Otto, Boisselle & Sklar, LLP

(57) ABSTRACT

A sensor system for sensing a moisture level of a working fluid includes a body housing a moisture indicator that changes color in the presence of moisture. The moisture indicator has a fixed position immersed in a path of fluid flow through the body. A light source is configured to transmit light through the moisture indicator to a color-sensing sensor of the sensor system. The sensor is separated from fluid flow through the system, and the system is configured to prevent external light from affecting the sensor. The moisture indicator is manually viewable where necessary. The sensor system also is configured to provide an electric signal corresponding to the color level of the moisture indicator, to generate an alarm signal with respect to a moisture level, to adjust for change in light intensity being sensed by the sensor, and to signify if the moisture indicator is damaged or has failed.

20 Claims, 11 Drawing Sheets

(51) Int. Cl.
*G01N 21/94* (2006.01)
*G01N 21/25* (2006.01)
*G01N 21/29* (2006.01)
*G01N 21/81* (2006.01)
*G01N 21/77* (2006.01)

(52) U.S. Cl.
CPC ..... *G01N 21/94* (2013.01); *G01N 2021/7763* (2013.01)

(56) References Cited

U.S. PATENT DOCUMENTS

| | | | | |
|---|---|---|---|---|
| 2002/0000120 A1* | 1/2002 | Dillon | ............... | G01F 23/2922 73/327 |
| 2007/0287989 A1* | 12/2007 | Crawford | ......... | A61M 5/16836 604/507 |
| 2010/0191051 A1* | 7/2010 | Miyake | ............. | A61B 1/00055 600/104 |
| 2011/0090488 A1* | 4/2011 | Andersen | ............. | G01R 33/072 356/213 |
| 2011/0197662 A1* | 8/2011 | McAlister | ............. | G01N 1/405 73/61.59 |
| 2014/0000345 A1* | 1/2014 | Wilson | ................... | E21B 43/38 73/31.07 |
| 2014/0205505 A1* | 7/2014 | Kirollos | ................ | G01N 31/22 422/119 |
| 2017/0065464 A1 | 3/2017 | Heil et al. | | |
| 2018/0017490 A1* | 1/2018 | Cader | ................... | G01N 21/59 |

OTHER PUBLICATIONS

Parker-Hannifin Corporation, Moisture and Liquid Indicators—Parker PSG Series, 3 pages printed, http://ph.parker.com/us/en/moisture-and-liquid-indicators-parker-psg-series.

* cited by examiner

MOISTURE SENSING SYSTEM

RELATED APPLICATIONS

This application claims the benefit of U.S. Provisional Application No. 62/516,745 filed Jun. 8, 2017, and the benefit of U.S. Provisional Application No. 62/607,462 filed Dec. 19, 2017, each of which is hereby incorporated herein by reference in its respective entirety.

FIELD OF INVENTION

The present invention relates generally to refrigeration units, freezing units, air conditioning units and similar heat transfer apparatuses that use refrigerant material as a working fluid, and more particularly to a sensor for detecting levels of moisture accumulation in the working fluid.

BACKGROUND

Cooling systems using refrigerant as a working fluid, such as refrigeration, freezing and air conditioning systems, are often susceptible to failure due to accumulation of moisture (water) in the refrigerant working fluid. Water vapor can enter such systems, where it is absorbed by the working fluid. In such systems, moisture accumulation can cause a host of issues, such as corrosion, acid formation, wear or breakdown of components, lower heat transfer efficiency, and other contaminant build up in the working fluid. For these reasons, monitoring of the working fluid for moisture level can be important.

Typically, a sensor system is employed that has a sight glass allowing viewing of a moisture indicator substrate exposed to the working fluid. When the substrate also is exposed to moisture, the substrate changes color. This monitoring method requires direct visual observation of the moisture indicator substrate and can prove to be ineffective where the sensor system is in a location that is hard to access, inaccessible, installed in a remote location, or not checked regularly.

Another moisture sensor system is disclosed in PCT/US1993/004747 that provides an output signal from the sensor system corresponding to the level of moisture contamination in a working fluid passing through the sensor system. The sensor system includes a cobalt bromide moisture indicator substrate that is immersed in the working fluid. An LED is used to illuminate the moisture indicator and a photodiode is used to measure the intensity of the light from the LED reflected off of the moisture indicator. The intensity is correlated to a level of moisture contamination and a corresponding signal output from the sensor system. However, the functioning of the sensor system includes numerous drawbacks including interference in the sensor system, such as contaminant in the fluid, affecting the reflected light. Other drawbacks include that the intensity of the measure reflected light typically changes with varying reflectance properties of the moisture indicator and with fluctuations in the light output of the LED, which is highly affected by temperature.

SUMMARY OF INVENTION

The present invention provides a sensor system for detecting a moisture level in a refrigerant working fluid that addresses many of the drawbacks of prior art sensor systems. The sensor system more accurately determines the color state of a moisture indicator via more direct reading of the color state of a respective indicator substrate while providing reduced interference with and interaction with light being read by a light sensor in the system. The accuracy is accomplished at least in part in view of a construction of the system providing for transmission of light from a light source through the moisture indicator to the light sensor.

The system generates an electrical output signal indicating moisture level, which can include an alarm, or subsequently can trigger an alarm, based on crossing of a moisture level threshold. The system also can adjust for change in light intensity being monitored and can indicate damage or failure of the moisture indicator substrate. A precise RGB color code corresponding to the color state of the moisture indicator substrate can further be provided, with each of the aforementioned outputs being transmittable by a wired or wireless connection.

For example, a sensor system according to the present invention includes a body insertable in a working fluid system of an external device, such as a heat transfer device. The body houses an indicator substrate that changes color when in the presence of moisture, which is immersed in a path of flow of working fluid through the body, and which has a fixed position in the body. A light source is configured to transmit light through the moisture indicator substrate to a color-sensing sensor of the sensor system. The color-sensing sensor is separated from working fluid flow through the sensor system, and the sensor system is configured to prevent external light from affecting the sensor. The moisture indicator substrate is manually viewable where necessary, although the sensor system is configured to provide automatic feedback. The sensor system can provide an electric signal corresponding to the color level of the moisture indicator substrate and can generate an alarm signal when a moisture level threshold corresponding to a particular color level has been reached or crossed. The system is further configured to adjust for change in light intensity being sensed by the sensor due to variations of the light source or temperature changes, and also can be configured to indicate if the moisture indicator substrate is damaged or has failed. The present invention further provides a method for accurately determining the moisture level of a working fluid.

According to one aspect of the invention, a sensor system for detecting moisture in a working fluid includes a body configured to receive the working fluid and having a longitudinal axis extending therethrough, a moisture indicator mounted in the body, a light source, and a sensor for receiving light passing from the moisture indicator to the sensor and initially transmitted by the light source. The moisture indicator is axially aligned along the longitudinal axis between the sensor and the light source.

The sensor system may be configured to direct light transmitted from the light source to the sensor through the moisture indicator.

The sensor system may be configured to direct light initially transmitted from the light source through a light guide towards the moisture indicator.

The sensor system may be configured such that the sensor detects incident light transmitted from the light source.

The moisture indicator may be a color-changing indicator, and the sensor is configured to sense the color of the color-changing moisture indicator.

The sensor may be a red-green-blue sensor.

The sensor system may further include a cap removably attachable to the body and housing the sensor, where the cap may be configured to block light external to the sensor system from the sensor.

The sensor system may further include a stem coupled to and received into the body. The stem may be disposed along the longitudinal axis between the light source and the moisture indicator, and the stem may have an opaque sheath circumferentially surrounding a transparent column for directing light from the light source to the moisture indicator.

According to another aspect of the invention, a sensor system for detecting moisture in a working fluid includes a body, a transparent surface arranged in the body, a moisture indicator mounted in the body at a first side of the transparent surface, a light source positioned at a second side of the transparent surface disposed opposite the first side of the transparent surface, and a light sensor disposed at the first side of the transparent surface. The light source is configured to transmit light in the body and through the transparent surface and the moisture indicator towards the light sensor.

The sensor system may be configured such that the sensor detects incident light transmitted from the light source.

The moisture indicator may be a color-changing indicator and the sensor may be configured to sense the color of the color-changing moisture indicator.

The sensor system may further include a stem coupled to and received into the body and having the transparent surface disposed at a first end of the stem and the light source disposed at a second end of the stem disposed opposite the first end of the stem.

The stem may include an opaque sleeve disposed about a transparent core. The transparent core may have the transparent surface and extending from the first end of the stem to the second end of the stem.

The sleeve may be made of metal and may be hermetically sealed about the transparent core.

The body may further include a bore extending between an inlet and outlet of the body. The transparent surface and moisture indicator may be disposed in the bore.

The sensor system may further include a cap removably attachable to the body and housing the sensor. The cap may be configured to block light external to the sensor system from the light sensor.

The sensor system may further include a cap disposed about the body and housing the sensor. The cap may be removable from the body to allow for viewing of the moisture indicator.

The moisture indicator may be coupled against the first side of the transparent surface by a coupling, and the coupling may prevent light leakage between the first side of the transparent surface and the moisture indicator.

According to yet another aspect of the invention, a method of detecting the color of a color-changing moisture indicator includes (a) mounting a color-changing moisture indicator at a first side of a transparent surface; (b) directing light from a light source through the color-changing moisture indicator from a second side of the transparent surface disposed opposite the first side of the transparent surface; and (c) detecting the color of the color-changing moisture indicator based on the color of the light that passes through the color-changing moisture indicator.

The method may further include transmitting the detected color of the color-changing moisture indicator by a wireless connection.

The foregoing and other features of the invention are hereinafter described in greater detail with reference to the accompanying drawings.

BRIEF DESCRIPTION OF THE DRAWINGS

The annexed drawings, which are not necessarily to scale, show various aspects of the disclosure.

DETAILED DESCRIPTION

The principles of the present disclosure have general application to measurement and detection of contaminant accumulation in a working fluid, and more particular application to measurement and detection of moisture accumulation, such as of water, in refrigeration units, freezing units, air conditioning units, and other heat transfer apparatuses that use a working fluid, such as a refrigerant.

A sensor system according to the present invention is fluidly coupled to an external device having a working fluid flowing through the device. The sensor system receives the working fluid through the sensor system and detects a moisture level in the working fluid, such as detecting a moisture level in a refrigerant working fluid of an external heat transfer device.

The sensor system includes a sensor that is configured to detect and determine the color state of a moisture indicator in the refrigerant working fluid, where the moisture indicator changes color in the presence of moisture, in particular water, accumulated in the refrigerant. The present invention also has application for detection and reading of a color state of an indicator that is present in working fluids other than refrigerants and for detection and reading of a color state of an indicator that changes color in response to presence of other contaminants accumulating in a working fluid.

Generally, a sensor system according to the present invention is configured to provide one or more of the following features, including: detecting a color state of a moisture indicator, correcting for variation in temperature of a sensor of the sensor system, correcting for variation in light detected by the sensor, transmitting a precise RGB color code of the moisture indicator at a time of reading of the color state of the moisture indicator, and providing an electrical signal with respect to crossing of a moisture accumulation threshold in the working fluid.

Figure 1:
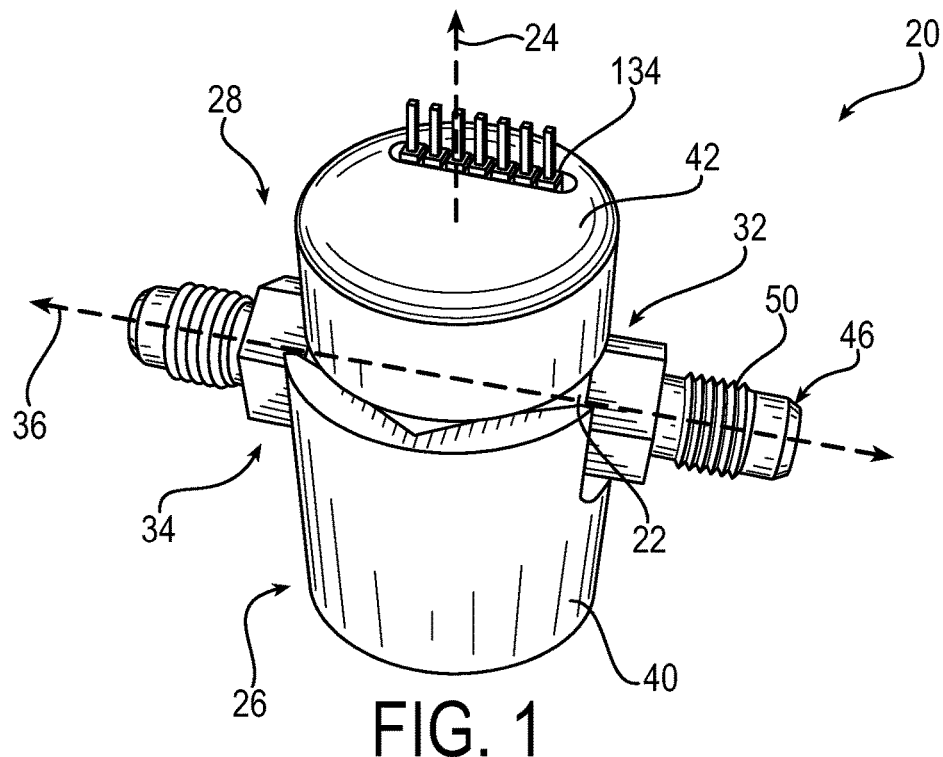
FIG. 1 is a perspective view of an exemplary sensor system for sensing a moisture level of a fluid flowing through the sensor system, in accordance with the present invention.
Figure 2:
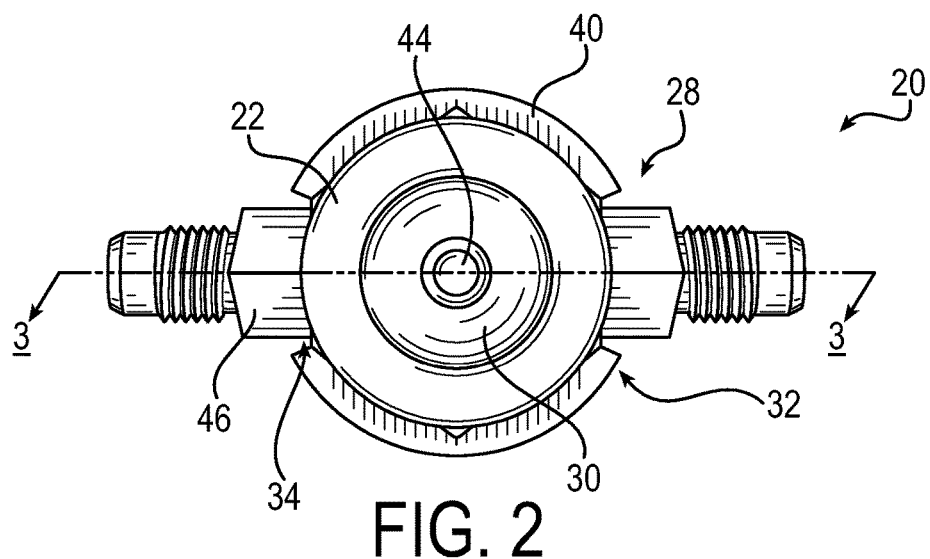
FIG. 2 is an elevated top view of the sensor system of FIG. 1.

Turning first to FIGS. 1 and 2, a sensor system according to the present invention is shown at 20 and includes a body 22 insertable in a working fluid system of an external device (not shown). The body 22 extends along a longitudinal body axis 24 between a first proximal end 26 and a second distal end 28 disposed opposite the first end 26. The body 22 defines a chamber 30, also herein referred to as a bore, and includes an inlet 32 and an outlet 34 each fluidly connected with the chamber 30. The depicted inlet 32 and outlet 34 are disposed opposite one another. A transverse body axis 36, along which flow of working fluid passes into and out of the body 22, extends through the chamber 30 and between the inlet 32 and the outlet 34. The transverse body axis 36 is generally transverse the longitudinal body axis 24, such as being orthogonal to the longitudinal body axis 24. In some embodiments, the inlet 32 and the outlet 34 may be disposed other than opposite one another.

A cover 40 is coupled to, such as press fit at, the first end 26 of the body 22. The cover 40 may provide for any one or more of protection, insulation, or mounting of the sensor system 20 relative to surrounding components of the external device with which the sensor system 20 is used. The cover 40 may contain recesses for constraining other components of the sensor system 22, such as a battery for powering at least a light source, as will be explained further.

Also included in the sensor system 20 is a cap 42 that is removably attachable to the second end 28 of the body 22. The depicted cap 42 is press fit onto the body 22. In other embodiments, a cap 42 may be threaded to the body 22 or connected by a fastener to the body 22. As shown in FIG. 2, the cap 42 may be selectively removed to allow for viewing of a moisture indicator 44 disposed in the chamber 30.

Connection couplings 46 are received into each of the inlet 32 and the outlet 34 of the body 22. A braze ring 48 (FIG. 3) is located between each coupling 46 and the body 22. The connection couplings 46 are coupled in the inlet 32 and the outlet 34, such as preferably by brazing, or alternatively the couplings 46 may be threaded to the body 22 or the body 22 and couplings 46 may each include corresponding quick connect features. The couplings 46 allow for connection of the body to tubing, piping, hoses, etc. of the working fluid transfer system of the respective external device. For example, the depicted couplings 46 include axially-spaced-apart ridges 50 for enabling retainment of tubing received onto the couplings 46. In some embodiments, the couplings 46 may be omitted from the sensor system 22 and may instead be part of the working fluid transfer system of the external device.

Figure 3:
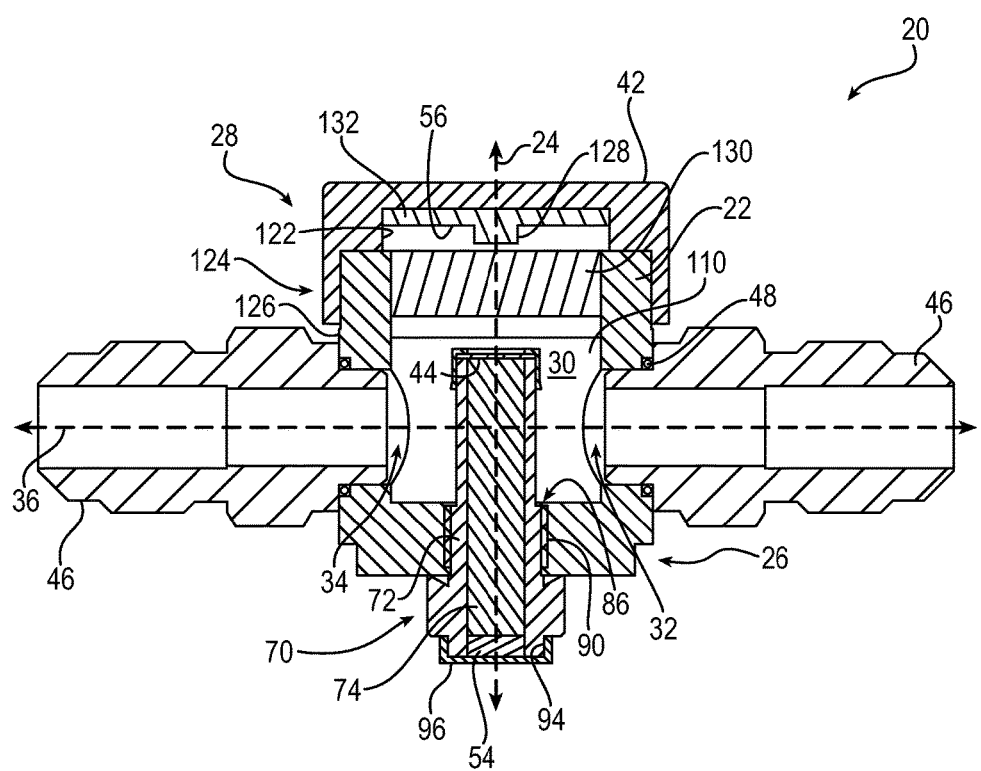
FIG. 3 is a cross-sectional view of the sensor system of FIG. 1, taken along the line 3-3 of FIG. 2.

Turning now to FIG. 3, the sensor system 20 is shown in cross-section along the line 3-3 of FIG. 2, with the cover 40 removed and depicting additional componentry of the sensor system 20. The moisture indicator 44 is mounted in the body 22. A light source 54 is mounted relative to the body 22 and relative to the moisture indicator 44 for illuminating the moisture indicator 44. A sensor 56 is positioned to receive light passing from the moisture indicator 44 to the sensor 56 that is initially transmitted by the light source 54. Generally, each of the sensor 56, the light source 54, and the moisture indicator 44 are supportively positioned relative to one another along the longitudinal body axis 24. The moisture indicator 44 is positioned between the sensor 56 and the light source 54 along the longitudinal body axis 24 to allow for transmission of light through the moisture indicator 44 towards the sensor 56. Accordingly, the sensor system 20 is configured to direct light through the moisture indicator 44 to the sensor 56, with the sensor 56 being configured to detect incident light passing from the moisture indicator 44 and transmitted by the light source 54.

Referring now in more detail to the components shown in FIG. 3, and first to the light source 54, the light source 54 may be any suitable light source for transmitting light, such as an LED transmitting white light, towards the moisture indicator 44. Use of a white light allows for efficient illumination of the moisture indicator 44. The light source 54 may include a power source, such as a battery. In some embodiments, the battery may not be disposed internal to the light source 54, but may be housed in a corresponding recess of the cover 40, adjacent the light source 54 when the cover 40 is received onto the first end 26 of the body 22.

The light source 54 is configured to turn on intermittently for a short duration, such as about a few seconds, to allow for the sensor 56 to detect the color state of the moisture indicator 44. For example, the sensor system 20 may be configured to turn on the light source 54 for a time in the range of about 0.2 seconds to about 5 seconds, or in the range of about 1 second to about 4 seconds, or for about 2 seconds. Due to the slow nature of moisture accumulation in typical working fluid transfer systems, the light source 54 generally does not need to be continuously transmitting light since continuous sensing of the moisture indicator 44 by the sensor 56 is not needed.

The depicted light source 54 includes a control hardware component, such as an application specific integrated circuit, a programable logic device, a memory device containing instructions, or the like for controlling the on/off intervals of the light source 54. For example, the light source 54 may be turned on one or more intervals a day. Other intervals and interval lengths other than indicated herein may be suitable.

In some embodiments, the light source 54 may be controlled by a control hardware component external to the sensor system 20. In such case, the light source 54 may have a connection terminal to allow for communicative connection to the external control hardware component, which communicative connection may be wired or wireless.

Figure 4:
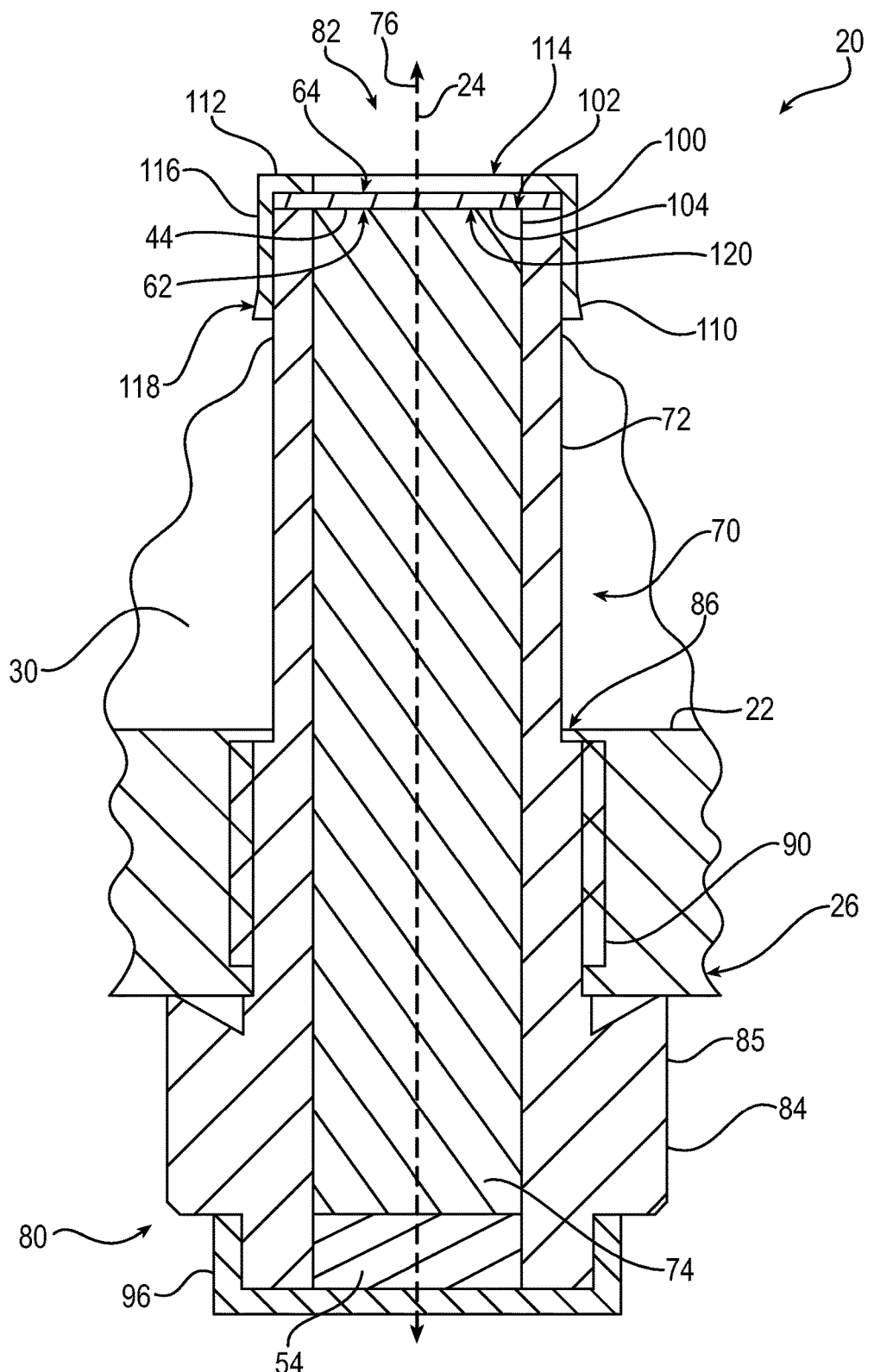
FIG. 4 is a partial enlarged view of the cross-sectioned sensor system illustrated in FIG. 3.

Referring now to both FIGS. 3 and 4, the moisture indicator 44, for being illuminated by the light source 54, includes a color-changing substrate that changes color in response to the presence of moisture in the working fluid in which the moisture indicator 44 is immersed. A typical moisture indicator gradually changes color over time due to the slow accumulation of moisture in a working fluid. An exemplary moisture indicator 44 is a sheet material, such as a cobalt bromide indicator paper.

The moisture indicator 44 is generally positioned in the body 22 such that light from the light source 54 may be transmitted through the moisture indicator 44. For example, light from the light source 54 is transmitted towards a proximal side 62 of the moisture indicator 44, through the moisture indicator 44, and from the distal side 64 of the moisture indicator 44 towards the sensor 56 (the distal side 64 being disposed opposite the proximal side 62).

To enable light from the light source 54 to pass through the moisture indicator 44, each of the light source 54 and the moisture indicator 44 are mounted to a stem 70 that is selectively coupled to the body 22. The stem 70 is generally cylindrical although other shapes may be suitable. The stem 70 serves as a light guide to direct light from the light source 54 and includes an opaque sheath 72, such as a metal sleeve, circumferentially surrounding a transparent core 74, such as a glass column. Each of the sleeve 72 and the transparent core 74 extend along a full longitudinal length of the stem 70 along a longitudinal stem axis 76. The illustrated longitudinal stem axis 76 is co-linear with the longitudinal body axis 24. The depicted transparent core 74 has a cylindrical shape and a uniform diameter along a full length of the core 74.

In some alternative embodiments, the transparent core 74 may not extend along a full longitudinal length of the stem 70. In some embodiments, the longitudinal stem axis 76 may be otherwise aligned relative to the longitudinal body axis 24, and may be parallel or transverse to the longitudinal body axis 24.

The sleeve 72 and the transparent core 74 are sealed relative to one another along a full longitudinal length of the stem 70, such as being hermetically sealed. This sealing prevents leakage of light from the light source 54 other than being directed through the transparent core 74. The sealing also prevents leakage of working fluid between the core 74 and the sleeve 72. In some embodiments, the sealing may only be at the opposite axial ends of the core 74 and the sleeve 72.

The sleeve 72 and the core 74 extend between a proximal end 80 of the stem 70, that is disposed external to the body 22, and a distal end 82 of the stem 70 disposed opposite the proximal end 80, and which is positioned internal to the body 22. A flange 84 of the sleeve 72 is disposed at the proximal end 80 and abuts the first end 26 of the body 22 when the stem 70 is received into the body 22. The flange 84 includes one or more flats 85 for allowing for grip of the flange 84 by a tool for coupling the stem 70 in a stem passage 86 at the first end 26 of the body 22. The stem passage 86 extends through the body 22 to the chamber 30 and is threaded for allowing threaded coupling of the stem 70, which includes corresponding stem threads 90. The stem 70 may be sealed to the body 22, such as to have a hermetic seal, such as using a metal-to-metal knife edge joint.

The light source 54 is mounted to the proximal end 80 of the stem 70 at a proximal axial end face 94 of the stem 70. The light source 54 is mounted adjacent the flange 84. A coupling 96 is coupled, such as threaded, to the proximal end 80, with the light source 54 contained between the coupling 96 and the proximal end 80 of the stem 70. In this way, the light source 54 is fixedly positioned relative to the transparent core 74, such as being centered along the longitudinal stem axis 76. In some embodiments, the coupling 96 may be at least partially welded to the stem 70.

At the distal end 82 of the stem 70, the stem 70 includes a generally planar distal axial end face 100 disposed opposite the proximal axial end face 94. The distal axial end face 100 includes a first side 102 of a transparent surface 104 of the transparent core 74. The moisture indicator 44 is mounted at the distal axial end face 100, such as directly against the axial end face 100. The moisture indicator 44 is sized to overlap at least a full area of the first side 102 the transparent surface 104, and as depicted, the moisture indicator 44 also is sized to overlap a full diameter of the distal axial end face 100. For example, the moisture indicator 44 has a circular shape corresponding to the cylindrical shape of the depicted stem 70, and has an outer diameter generally equal to an outer diameter of the stem 70 at the distal axial end face 100.

The moisture indicator 44 is coupled adjacent the first side 102 by an indicator coupling 110. The stem 70 and the coupling 110 are maintained in engagement via a press fit, although other methods of engagement may be suitable in other embodiments, such as by threading, welding, brazing or use of a fastener or spring clip. Coupling of the moisture indicator 44 to the stem 70 by the coupling 110, and threading of the stem 70 to the body 22, allows for the moisture indicator 44 to have a fixed position within the body 22 immersed within the flow of the working fluid between the inlet 32 and the outlet 34.

The coupling 110 is circular in shape to correspond to the cylindrical shape of the depicted stem 70. The coupling 110 includes a face portion 112 disposed at the distal axial end face 100 of the stem 70. The face portion 112 extends from an outer periphery of the sleeve 72 radially inwardly to a light opening 114 in the face portion 112. The light opening 114 is sized to have a diameter generally equivalent to an outer diameter of the transparent surface 104 of the core 74 at the distal axial end face 100, with the face portion 112 generally fully overlapping the sleeve 72 at the distal axial end face 100. The light opening 114 is thus generally centered on the distal axial end face 100 and centered on the longitudinal stem axis 76.

An outer peripheral indicator edge of the moisture indicator 44, preferably having a circular shape, is sandwiched between the face portion 112 and the distal axial end face 100. The outer peripheral indicator edge has a diameter generally equivalent to an outer diameter of the stem 70 at the outer periphery of the stem 70.

A peripheral wall 116 of the coupling 104 extends from the face portion 112, such as orthogonally from the face portion 112, about the periphery of the sleeve 72 of the stem 70 and provides for the press fit of the coupling 110 with the stem 70. For example, a full outer circumference at a proximal end 118 of the peripheral wall 116 is disposed against the sleeve 72.

This contiguous engagement of the coupling 110 with the stem 70, in combination with the shape and positioning of each of the face portion 112 and the moisture indicator 44, allows for the coupling 110 to restrict or altogether prevent leakage of light from between the first side 102 of the transparent surface 104 and the proximal side 62 of the moisture indicator 44 into the chamber 30. Rather, light received at the proximal side 62 of the moisture indicator 44 disposed at the first side 102 of the transparent surface 104 is directed through the moisture indicator 44 and through the light opening 114 towards the sensor 56. Accordingly, by the aforementioned press fit of the coupling 110 and shape and positioning of the coupling 110 and the moisture indicator 44, the sensor system 20 is configured to direct substantially all light transmitted through the moisture indicator 44 in a direction towards the sensor 56.

As used herein, the term "substantially all light" refers to a quantity of light transmitted through the moisture indicator 44. For example, an amount of light in the range of about 100 percent to about 80 percent, or in the range of about 98 percent to about 82 percent, or in the range of about 95 percent to about 85 percent, or about 90 percent of light passing through the moisture indicator 44 may be directed towards the sensor 56. One of ordinary skill will understand that a small quantity of light may otherwise escape or be directed other than towards the sensor 56 or through the moisture indicator 44, such as being reflected back towards the light source 54.

Further, the construction of the stem 70 and the positioning of the light source 54 and the moisture indicator 44 relative to the stem 70 allows the sensor system 20 to be configured to direct substantially all light transmitted from the light source 54 through the moisture indicator 44. For example, the stem 70 is positioned along the longitudinal body axis 24 between the moisture indicator 44 and the light source 54. The light source 54 is positioned at a second side 120 of the transparent surface 104 (opposite the first side 100) to transmit light only through the transparent core 74 and thus provide backlighting of the color changing moisture indicator 44. The light transmitted into the core 74 is directed along the full length of the core 74 due to the positioning of the outer sleeve 72 and hermetic sealing of the sleeve 72 and the core 74.

As used herein, the term "substantially all light" refers to a quantity of light transmitted from the light source 54. For example, an amount of light in the range of about 100 percent to about 80 percent, or in the range of about 98 percent to about 82 percent, or in the range of about 95 percent to about 85 percent, or about 90 percent of light transmitted from the light source 54 is directed through the moisture indicator 44. One of ordinary skill will understand that a small quantity of light may otherwise escape or be directed other that towards the sensor 56 or through the transparent core 74, such as being reflected back towards the light source 54 or being directed external to the transparent core 74 at a periphery of the transparent core 74 at the proximal axial end face 94.

Turning now to the sensor 56, the sensor 56 is disposed at the first side 100 of the transparent surface 102 at the distal side 64 of the moisture indicator 44. As shown, and as previously indicated, the sensor 56 is located along the longitudinal body axis 24 such that the moisture indicator 44 is disposed between the sensor 56 and the light source 54 along the longitudinal body axis 24. In this way, the sensor 56 is positioned to receive incident light transmitted generally from the moisture indicator 44—light that has passed through, rather than reflecting off of, the moisture indicator 44.

The sensor 56 is housed inside a recess 122 of the cap 42 and is located outside of the flow of the working fluid through the chamber 30 of the body 22. The sensor 56 is not immersed in the body 22 and is fixedly positioned relative to the moisture indicator 44 upon attachment of the cap 42 to the second distal end 28 of the body 22. The sensor 56 may be attached by any suitable means to the cap 42, such as by adhesive, welding, or a fastener.

When the cap 42 is selectively attached to the body 22, a full circumference of the cap 42 at a proximal end 124 of the cap is disposed against an outer surface 126 of the body 22. In this way, the cap 42 is configured to block light external to the sensor system 20 from the sensor 56, similar to the coupling 110 preventing light leakage from between the moisture indicator 44 and the transparent surface 104. The blocking of external light enables a more accurate reading of incident light transmitted from the moisture indicator 44 to the sensor 56.

With the cap 42 selectively attached to the body 22, the proximal-most aspect of the sensor—a light receiving portion 128, such as a photodiode—is disposed adjacent a sight glass 130 sealing the first distal end 26 of the body 22 and at least partially defining the chamber 30. In this way, the cap 42 is configured to minimize distance incident light needs to travel from the moisture indicator 44 to the sensor 56. The sight glass 130, separates the sensor 56 from the working fluid in the chamber 30 and is sealed, such as hermetically sealed, about its periphery to the body 22, which is preferably metal, such as aluminum or steel. Accordingly, it will be appreciated that via selective removal of the cap 42 and the sensor 56, the moisture indicator 44 may be manually viewed (by a user) through the sight glass 130, such as to verify the color state of the moisture indicator 44 output by the sensor 56, to be further discussed.

The alignment of the cap 42 also provides for alignment of the sensor 56 centered at the longitudinal body axis 24. In particular, in the illustrated embodiment of FIG. 3, each of the light source 54, the moisture indicator 44, the light opening 114, and the sensor 56 are centered along the longitudinal body axis 24, with the longitudinal body axis 24 intersecting each of the light source 54, the moisture indicator 44, the light opening 114, and the sensor 56. This alignment provides for a relatively straight path from the light source 54 to the sensor 56, enhancing the accuracy of the sensing of the transmitted light by the sensor 56.

In other embodiments, it is noted that each of the sensor 56, the light source 54, the moisture indicator 44, and the light opening 114 do not need to be centered relative to one another or along a common longitudinal axis of the body, such as the longitudinal body axis 24. For example, one or more of these components may be offset laterally from one another, such as in a direction orthogonal to the longitudinal body axis 24.

Turning now to more particular aspects of the sensor 56 and to its functioning, the sensor 56 is a light sensor, and is configured to sense the color of the color-changing moisture indicator 44. For example, the sensor 56 may be a red-green-blue sensor. As the moisture indicator 44 is exposed to higher moisture levels, the reflectance and transmittance properties of the moisture indicator 44 change. This shift is detected by the sensor 56 as a shift in the primary wavelength of the incident light transmitted from the moisture indicator 44. A magnitude of the shift is converted to a digital signal by logic of the sensor 56 and is further communicated via a transmission element of the sensor 56.

To control the sensor 56, the sensor 56 includes a control circuit, such as a programmable logic circuit 132, operatively connected to the light receiving portion 128, of the sensor 56. A transmission element (not shown) may further be attached to the programmable logic circuit 132, such as within the cap 42, or attached to an electrical connection 134 shown in FIG. 1, which is operatively connected to the programmable logic circuit 130. A suitable transmission element may allow for wired or wireless connection of the sensor system 20 to an external processor having a display operatively connected to the processor. For example, the programmable logic circuit 132 may be configured to transmit data from the sensor 56 via the transmission element through any suitable network connection, such as cellular, wifi, ethernet, Bluetooth, token ring, Zigbee, etc.

Figure 5:
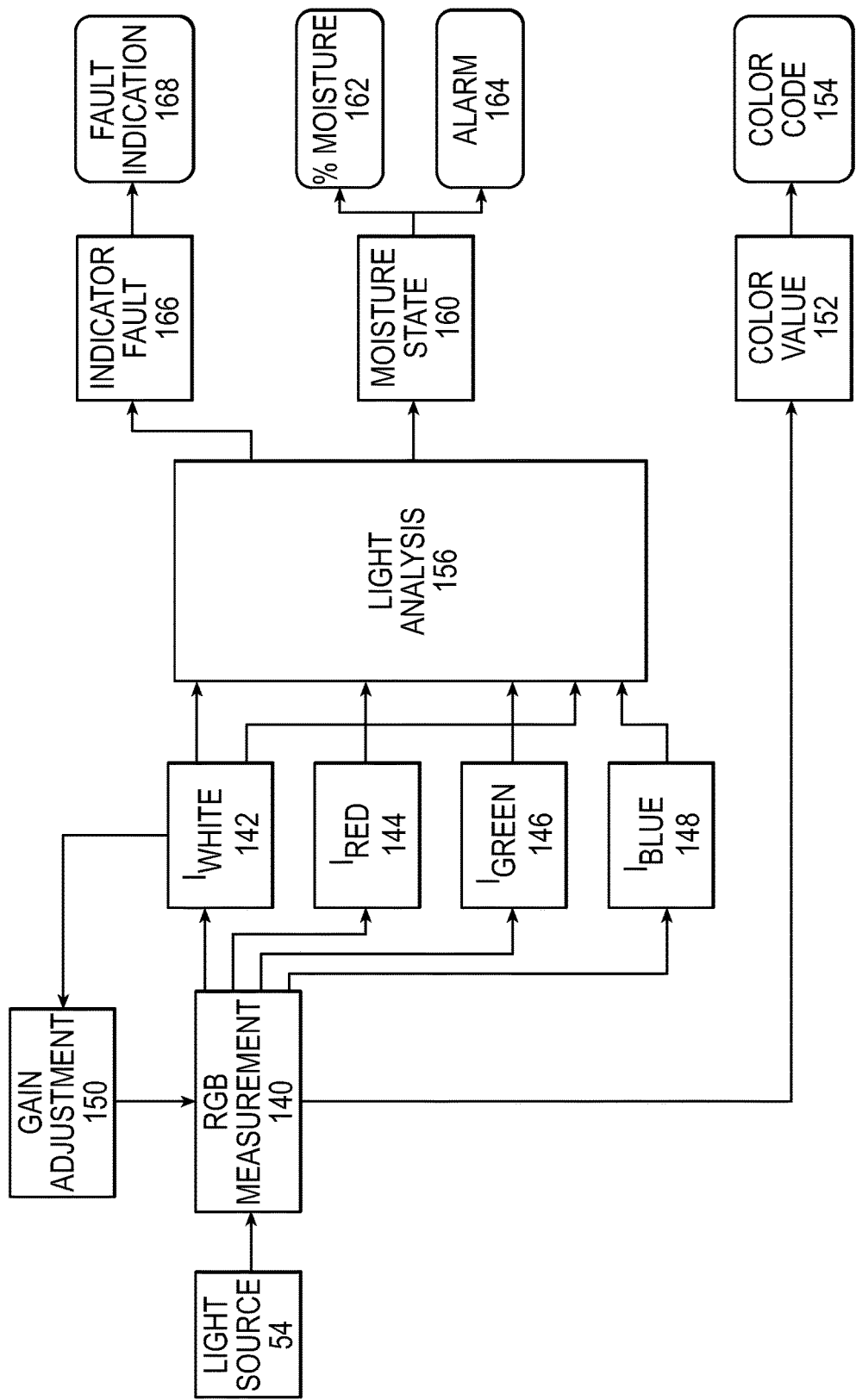
FIG. 5 is a schematic illustration of the logic of a color-sensing sensor of the sensor system of FIG. 1.

Turning to FIG. 5, an exemplary logic of the sensor 56 is schematically depicted. As depicted, the light source 54 provides light which is received by the sensor 56. At box 140, the sensor 56 is configured via the logic to take a red-green-blue measurement of the color state of the moisture indicator 44 via the incident light received at the sensor 56 from the moisture indicator 44. The RGB measurement is broken down via the logic into separate color intensity measurements, including white light intensity (box 142), red light intensity (box 144), green light intensity (box 146), and blue light intensity (box 148). In view of the white light intensity, the sensor 56 is configured to provide for gain adjustment at box 150, in view of varying white light intensity transmitted from the light source 54. The sensor 56 also is configured to adjust for variations in temperature of the sensor 56 as part of the gain adjustment. Temperature variation can affect both the light output by the light source 54 and the RGB measurement taken. By adjusting for both temperature and white light intensity, fluctuations in RGB measurement can be minimized, leading to more consistent reading of the color state of the moisture indicator 44 from measurement to measurement.

The sensor 56 is configured to provide numerous output data. For example, the sensor 56 is configured to convert the RGB measurement of box 140 into a color value at box 152, and to provide an electric signal corresponding to the precise color code of the moisture indicator 44 at box 154. The electrical signal of box 154 may also include an accurate color depiction of the color code, which can then be displayed on the aforementioned display, such as a display connected to the external device or a display of a computer monitor, watch, phone, tablet, etc.

The sensor 56 also is configured to make an analysis of the light received at the sensor 56 at box 156. For example, in one embodiment, a comparison of the red light intensity and white light intensity, or a comparison of the green light intensity and white light intensity, may be used. In such embodiment the comparisons are used to determine the relative green and red light color shifts of light emanating from the moisture indicator 44, corresponding to a color change of the substrate of the moisture indicator 44.

The green and red light color shifts are thus calculated as corresponding to a particular moisture state (also referred to as a color state) of the moisture indicator 44 at box 160. In other embodiments, alternative light colors and color shifts may be analyzed, such as where an alternatively colored moisture indicator is used. Subsequently the sensor 56 provides an output electrical signal corresponding to the percent moisture of the working fluid system at box 162 (corresponding to the particular moisture state of the moisture indicator 44), based on stored data regarding working fluid of the working fluid system, such as refrigerant type, volume, etc.

The sensor 56 is configured to determine if the moisture state provided at box 160 has crossed a moisture level threshold corresponding to a particular color level of the moisture indicator 44. Where the threshold has been crossed, an electrical signal is output at box 164 from the sensor 56 that includes a visual or audible alarm, thereby indicating failure of the working fluid due to the level of moisture having accumulated in the working fluid.

Additionally, the sensor 56 is configured to recognize at box 166 whether the results of the light analysis conducted at box 156 are indicative of a non-typical color state of the normal color-change progression of the moisture indicator 44. Where the analysis results in determination of a shift from a typical color-change progression of the specific moisture indicator being used, such as where color intensity comparisons are shifted, thus indicating a fault in or failure of the moisture indicator 44, the sensor 56 may be configured to provide such finding to the user. A fault indication, such as a visual or audible alarm, may be output as a corresponding electrical signal at box 168. A fault in the moisture indicator may be caused by a manufacturing defect or damage to the moisture indicator 44, such as being caused during installation of the coupling 110 over the moisture indicator 44 and the stem 70.

In view of the capabilities of the sensor 56, and the arrangement of the sensor 56, the light source 54, and the moisture indicator 44 relative to one another in the sensor system 20, the sensor system 20 provides one or more benefits over conventional moisture sensing systems. As noted with respect to FIG. 5, the sensor system 56 is configured to provide an accurate reading of the color state of the moisture indicator 44 and to output a color code corresponding to the color state, a percent moisture accumulation corresponding to the color state, and an alarm representing failure of the working fluid based on crossing of a color state threshold of the moisture indicator 44. Gain adjustment allows for consistent measurement of the color state of the moisture indicator by adjusting for output intensity of the light source 54 and temperature of the sensor system 20.

With respect to the arrangement of the components of the sensor system 20, the moisture indicator 44 is disposed between the light source 54 and the sensor 56 such that the moisture indicator 44 is backlit to provide more direct incident light from the moisture indicator 44 to the sensor 56. The backlighting also assists in accurate manual viewing of the moisture indicator 44 when the sensor system 20 is placed in a dark environment. Use of the stem 70 provides for a fixed position of the moisture indicator 44 in the body 22, while also allowing for easy change of the moisture indicator 44 by selective removal of the stem 70 from the body 22.

Figure 6:
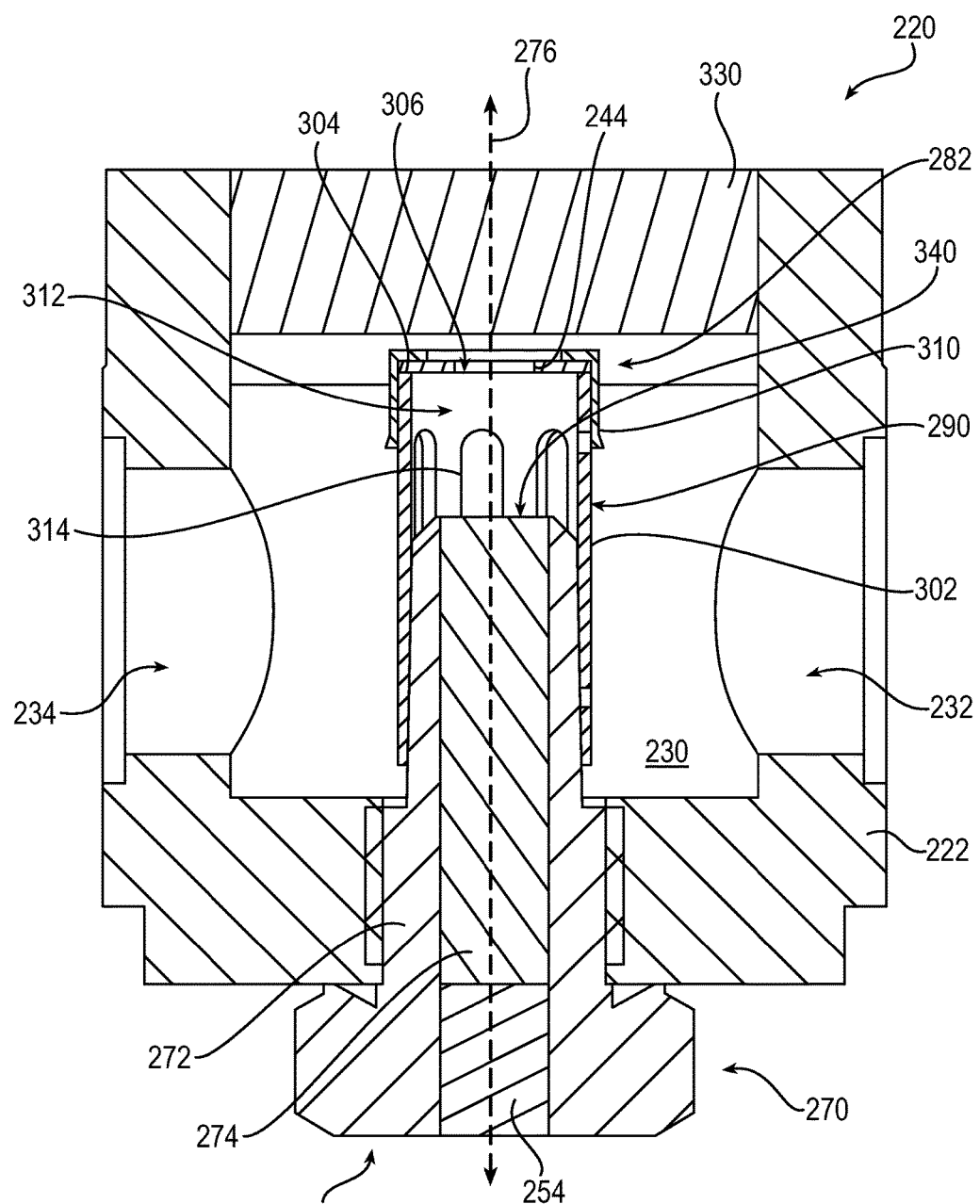
FIG. 6 is a partial view of another cross-sectioned exemplary sensor system, in accordance with the present invention.

Turning now to FIG. 6, an exemplary embodiment of the sensor system is shown at 220. The sensor system 220 is substantially the same as the above-referenced sensor system 20, and consequently the same reference numerals but indexed by 200 are used to denote structures corresponding to similar structures in the sensor system 220. In addition, the foregoing description of the sensor system 20 is equally applicable to the sensor system 220 except as noted below. Moreover, it will be appreciated upon reading and understanding the specification that aspects of the sensor systems 20 and 220 may be substituted for one another or used in conjunction with one another where applicable.

The sensor system 220 is shown in cross-section, the stem 270 includes a sleeve 272 and the transparent core 274 sealed relative to one another along a partial longitudinal length of the stem 270, such as being hermetically sealed. The sleeve 272 and the core 274 extend between a proximal end 280 of the stem 270, that is disposed external to the body 222, and a distal end 282 of the stem 270 disposed opposite the proximal end 280, and which is positioned internal to the body 222. The light source 254 is mounted to the proximal end 280.

A stem extension 290 of the stem 270 is mounted to the distal end 282 of the sleeve 272. In the illustrated embodiment, a proximal portion of the stem extension 290 extends about at least a portion of the outer periphery of a distal portion of the sleeve 272. The stem extension 290 includes a radially outer wall 302 that extends distally axially along the longitudinal axis 276 from the sleeve 272. The radially outer wall 302 extends to a generally planar distal axial end face 304 having an opening 306, where the moisture indicator 244 is mounted at the distal axial end face 304 by the indicator coupling 310. The distal axial end face 304 is axially spaced from the sleeve 272 and the core 274 along the longitudinal axis 276 defining a gap 312 therebetween. Light from the light source 254 is transmitted through the core 274, across the gap 312, and through the opening 306, to the moisture indicator 244.

The radially outer wall 302 includes a plurality of passages 314 extending fully through the radially outer wall 302 from the gap 312 to the chamber 230 in which the stem 270 is received. The illustrated passages 314 are equally circumferentially spaced form one another about the wall 302, although other spacing may be used where suitable. The passages 314 allow for direct illumination of radially inner walls of the chamber 230 and of flow passing directing between the inlet 232 and outlet 234 of the body 222, as compared to reflected illumination of these aspects by light transmitted through the moisture indicator 244 and reflected off the sight glass 330 or cap (not shown). In this way, the passages 314 allow for increased illumination of the chamber 230 as compared to the sensor system 20.

Figure 7:
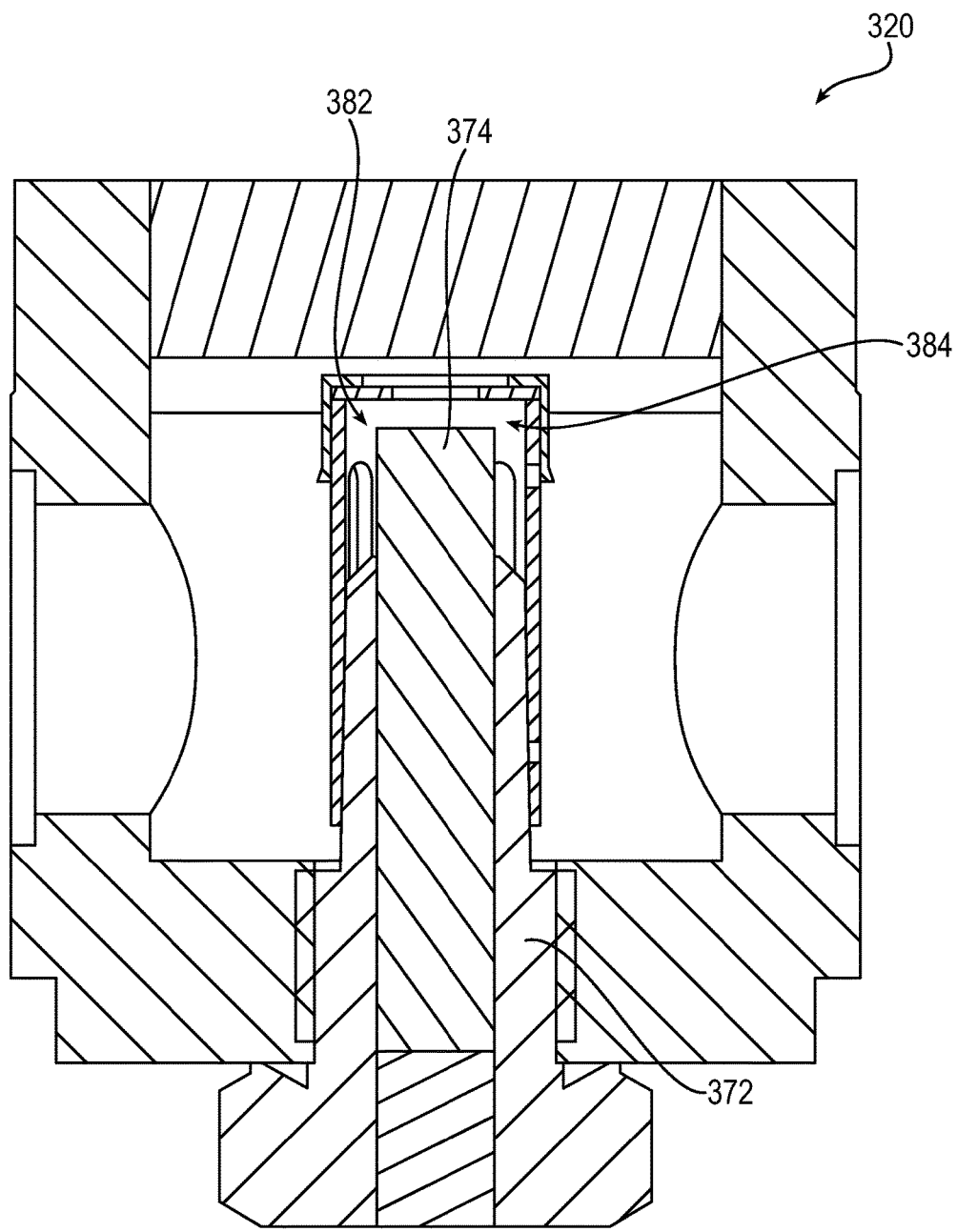
FIG. 7 is a partial view of yet another cross-sectioned exemplary sensor system, in accordance with the present invention.

As shown in FIG. 6, the core 274 and the sleeve 272 extend to a shared distal end face 340. Alternatively, in FIG. 7, the sensor system 320 is depicted with the core 374 extending beyond the distalmost portion of the sleeve 372 to a distal end 382 of the core 274. The extended portion of the core 374 may allow for increased direction of light to the moisture indicator 344 through the gap 384 as compared to the stem 270 of FIG. 6.

Turning now to FIGS. 8 to 13, additional exemplary embodiments of sensor systems are depicted. These sensor systems are substantially the same as the above-referenced sensor systems 20, 220, and 320, and consequently the same reference numerals but indexed respectively are used to denote structures corresponding to similar structures in the sensor systems 20, 220, and 320. In addition, the foregoing descriptions of the sensor systems 20, 220, and 320 are equally applicable to these sensor systems except as noted below. Moreover, it will be appreciated upon reading and understanding the specification that aspects of each of the sensor systems described herein may be substituted for one another or used in conjunction with one another where applicable.

Turning generally to the embodiments of FIGS. 8 to 13, each respective sensor system includes a detachable/attachable light source. In each of the embodiments, although not shown, a cap may be provided for the proximal end of the body respective body, which may be removed prior to engagement of the separate light source.

Figure 8:
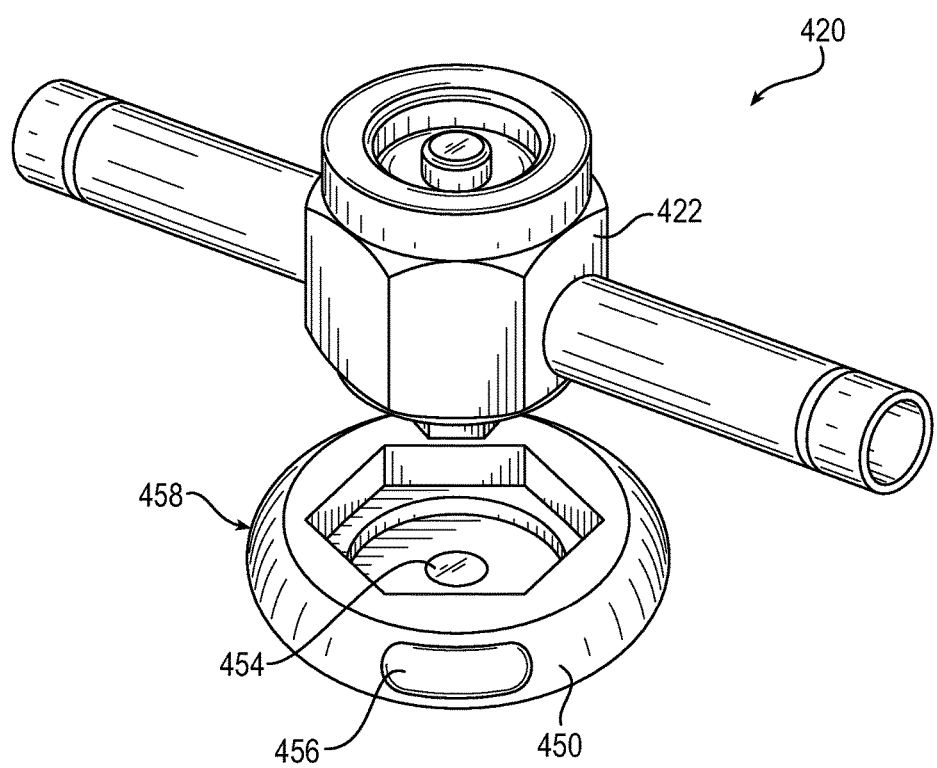
FIG. 8 is a perspective view of another exemplary sensor system, in accordance with the present invention.

Referring first to FIG. 8, a sensor system 420 includes a light indicator 450 having a light source 454 and included power source (not specifically shown) for powering the light source 454. The light indicator 450 is attachable to the proximal end of the body 422 and includes an actuation element 456 for activating/deactivating the light source 454. The light indicator 450 includes a cavity 457 that receives a proximal end of the body 422 and an outer peripheral surface 458 that is configured to be slip-resistant, such as including a slip-resistant material.

Figure 9:
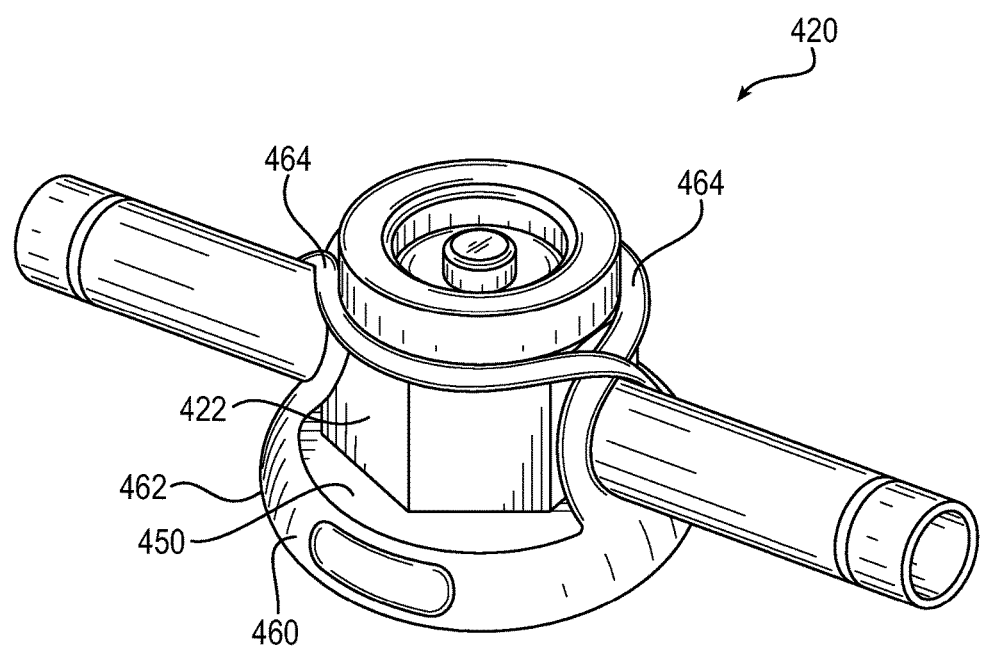
FIG. 9 is a perspective view of the sensor system of FIG. 8, further including a retention element.
Figure 10:
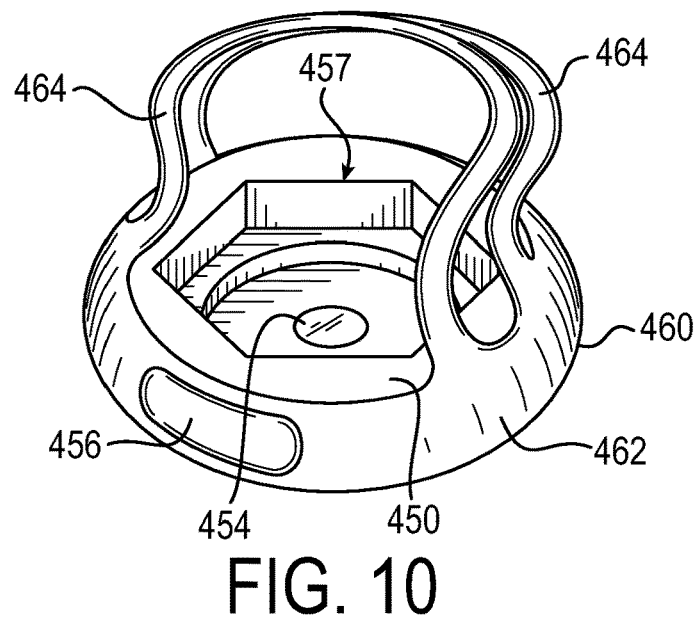
FIG. 10 is a perspective view of the indicator light and retention element of FIG. 9 shown separate from a remainder of the sensor system.

Turning now to FIGS. 9 and 10, the sensor system 420 of FIG. 8 is depicted further including an attachment element 460 for maintaining the light indicator 450 in engagement with the body 422. The light indicator 450 may include the slip-resistant outer peripheral surface 458 or the surface 458 may be omitted. The attachment element 460 includes a main body portion 462 that receives at least a portion of an outer periphery of the light indicator 450. A pair of opposed loop portions 464 extend from the main body portion 462. The loop portions 464 are configured to wrap about a distal end of the body 422, such as crossing over one another to engage opposite lateral sides 464 and 466 of the body 422. In the depicted embodiment, at least the loop portions 464 include an elastic material, where a stretching of the loop portions 464 to engage the distal end of the body 422 tensions the light indicator 450 against the proximal end of the body 422 where the light indicator 450 is received by the main body portion 462. As depicted, the main body portion 462 also may include an elastic material for allowing a tight engagement with the light indicator 450.

Figure 11:
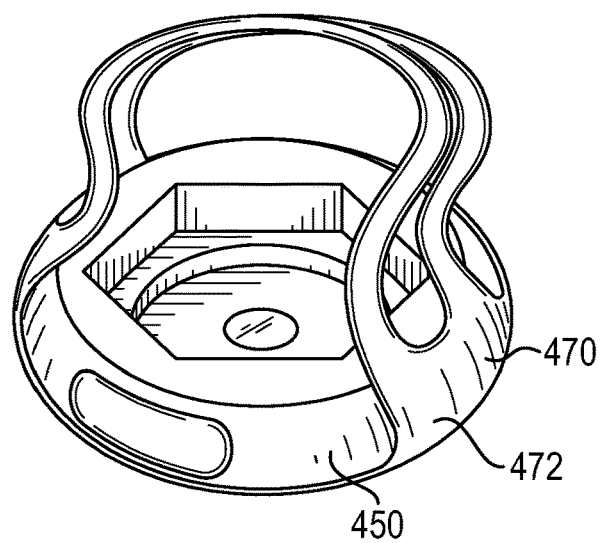
FIG. 11 is a perspective view of another indicator light and retention element for use in the sensor system of FIG. 9.

Turning to FIG. 11, the light indicator 450 is depicted with an alternative embodiment of an attachment element 470 that includes a reduced main body portion 472 as compared to the main body portion 462 of the attachment element 460 illustrated in FIGS. 9 and 10.

Figure 12:
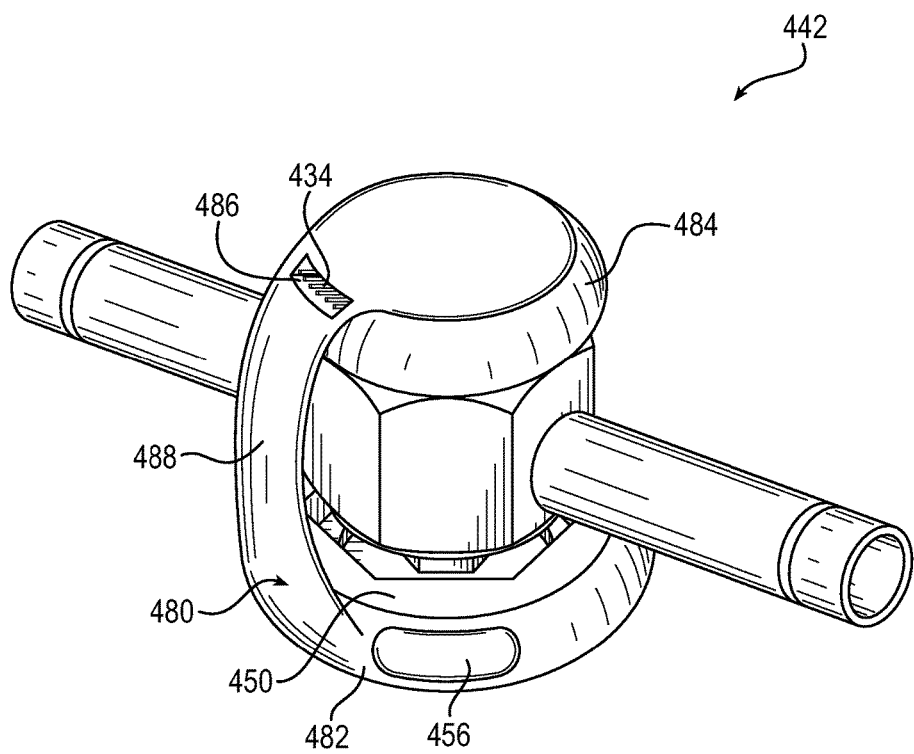
FIG. 12 is a perspective view of the sensor system of FIG. 8, further including another retention element.

Referring next to FIG. 12, yet another alternative attachment element 480 is depicted. The attachment element 480 includes a main body portion 482 that receives the light indicator 450. A secondary body portion 484 is disposed about a cap 442. The secondary body portion 484 includes an opening 486 for allowing access to the electrical connection 434. An extension portion 488 extends between the main body portion 482 and the secondary body portion 484. At least the extension portion 488 may include an elastic material.

Figure 13:
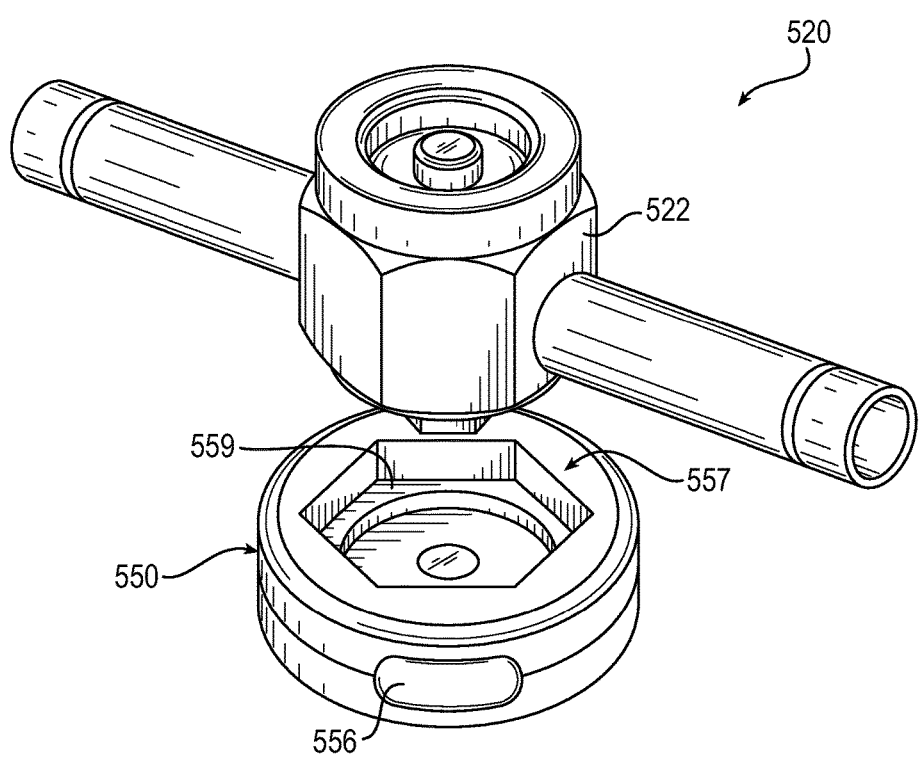
FIG. 13 is a perspective view of yet another exemplary sensor system, in accordance with the present invention.

Turning now to FIG. 13, yet another embodiment of a sensor system is depicted. The sensor system 520 includes a light indicator 550 having a light source 554 and an actuation element 556 for activating/deactivating the light source 554. The light indicator 550 includes a magnetic element 559 for magnetically engaging a corresponding magnetic material of the body 522 to maintain engagement between the light indicator 550 and the body 522. The magnetic element 559 is disposed in a cavity 557 of the light indicator 550 that receives the proximal end of the body 522. In other embodiments a magnetic element may be otherwise suitably disposed at the light indicator 550.

Any of the light indicator embodiments of FIGS. 8-13 may include a magnetic element for maintaining engagement between the respective light indicator and the respective body, where the body includes a corresponding magnetic material.

In summary, a sensor system 20, 220, 320, 420, 520 for sensing a moisture level of a working fluid includes a body 22, 222, 422, 522 housing a moisture indicator 44, 244, 344 that changes color in the presence of moisture. The moisture indicator 44, 244, 344 has a fixed position immersed in a path of fluid flow through the body 22, 222, 422, 522. A light source 54, 254, 454, 554 is configured to transmit light through the moisture indicator 44, 244, 344 to a color-sensing sensor 56 of the sensor system 20, 220, 320, 420, 520. The sensor 56 is separated from fluid flow through the system 20, 220, 320, 420, 520, and the system 20, 220, 320, 420, 520 is configured to prevent external light from affecting the sensor 56. The moisture indicator 44, 244, 344 is manually viewable where necessary. The sensor system 20, 220, 320, 420, 520 also is configured to provide an electric signal corresponding to the color level of the moisture indicator 44, 244, 344, to generate an alarm signal with respect to a moisture level, to adjust for change in light intensity being sensed by the sensor 56, and to signify if the moisture indicator 44, 244, 344 is damaged or has failed.

The present invention is further direct to a method of detecting the color of a color-changing moisture indicator 44, 244, 344. The method includes the steps of (a) mounting a color-changing moisture indicator 44, 244, 344 at a first side 102 of a transparent surface 104, (b) directing light from a light source 54, 254, 454 through the color-changing moisture indicator 44, 244, 344 from a second side 120 of the transparent surface 104 disposed opposite the first side 102 of the transparent surface 104, (c) detecting the color of the color-changing moisture indicator 44, 244, 344 based on the color of the light that passes through the color-changing moisture indicator 44, 244, 344, and (d) transmitting the detected color of the color-changing moisture indicator 44, 244, 344 by a wireless connection.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sensor system for detecting moisture in a working fluid, the sensor system comprising:
    a body configured to receive the working fluid and having a longitudinal axis extending therethrough;
    a moisture indicator mounted in the body;
    a light source; and
    a sensor for receiving light passing from the moisture indicator to the sensor and initially transmitted by the light source,
    wherein the moisture indicator is axially aligned along the longitudinal axis between the sensor and the light source.

2. The sensor system of claim 1, wherein the sensor system is configured to direct light transmitted from the light source to the sensor through the moisture indicator.

3. The sensor system of claim 2, wherein the sensor system is further configured to direct light initially transmitted from the light source through a light guide towards the moisture indicator.

4. The sensor system of claim 1, wherein the sensor system is configured such that the sensor detects incident light transmitted from the light source.

5. The sensor system of claim 1, wherein the moisture indicator is a color-changing indicator, and the sensor is configured to sense the color of the color-changing moisture indicator.

6. The sensor system of claim 1, wherein the sensor is a red-green-blue sensor.

7. The sensor system of claim 1, further including a cap removably attachable to the body and housing the sensor, and wherein the cap is configured to block light external to the sensor system from the sensor.

8. The sensor system of claim 1, further including a stem coupled to and received into the body, the stem disposed along the longitudinal axis between the light source and the moisture indicator, and the stem having an opaque sheath circumferentially surrounding a transparent column for directing light from the light source to the moisture indicator.

9. A sensor system for detecting moisture in a working fluid, the sensor system comprising:
    a body;
    a transparent surface arranged in the body;
    a moisture indicator mounted in the body at a first side of the transparent surface;
    a light source positioned at a second side of the transparent surface disposed opposite the first side of the transparent surface; and
    a light sensor disposed at the first side of the transparent surface, wherein the light source is configured to transmit light in the body and through the transparent surface and the moisture indicator towards the light sensor.

10. The sensor system of claim 9, wherein the sensor system is configured such that the sensor detects incident light transmitted from the light source.

11. The sensor system of claim 9, wherein the moisture indicator is a color-changing indicator and the sensor is configured to sense the color of the color-changing moisture indicator.

12. The sensor system of claim 9, further including a stem coupled to and received into the body and having the transparent surface disposed at a first end of the stem and the light source disposed at a second end of the stem disposed opposite the first end of the stem.

13. The sensor system of claim 12, wherein the stem includes an opaque sleeve disposed about a transparent core, the transparent core having the transparent surface and extending from the first end of the stem to the second end of the stem.

14. The sensor system of claim 13, wherein the sleeve is made of metal and is hermetically sealed about the transparent core.

15. The sensor system of claim 9, wherein the body further includes a bore extending between an inlet and outlet of the body, with the transparent surface and moisture indicator disposed in the bore.

16. The sensor system of claim 9, further including a cap removably attachable to the body and housing the sensor, and wherein the cap is configured to block light external to the sensor system from the light sensor.

17. The sensor system of claim 9, further including a cap disposed about the body and housing the sensor, the cap being removable from the body to allow for viewing of the moisture indicator.

18. The sensor system of claim 9, wherein the moisture indicator is coupled against the first side of the transparent surface by a coupling, and wherein the coupling prevents light leakage between the first side of the transparent surface and the moisture indicator.

19. A method of detecting the color of a color-changing moisture indicator, the method comprising:
    mounting a color-changing moisture indicator at a first side of a transparent surface;
    directing light from a light source through the color-changing moisture indicator from a second side of the transparent surface disposed opposite the first side of the transparent surface; and
    detecting, by a light sensor, the color of the color-changing moisture indicator based on the color of the light that passes through the color-changing moisture indicator.

20. The method of claim 19, further including transmitting the detected color of the color-changing moisture indicator by a wireless connection.

* * * * *